United States Patent [19]
Itoh et al.

[11] Patent Number: 5,198,369
[45] Date of Patent: Mar. 30, 1993

[54] SAMPLE MEASURING METHOD USING AGGLOMERATION REACTION OF MICROCARRIERS

[75] Inventors: Yuuji Itoh; Michiyo Itoh, both of Chigasaki; Yoshiyuki Touge, Kawasaki; Atsushi Saitou, Yokohama; Tatsuya Yamazaki, Zushi, all of Japan

[73] Assignee: Canon Kabushiki Kaisha, Tokyo, Japan

[21] Appl. No.: 687,627

[22] Filed: Apr. 19, 1991

[30] Foreign Application Priority Data

Apr. 25, 1990 [JP] Japan ................... 2-109328
May 31, 1990 [JP] Japan ................... 2-143729
Jul. 6, 1990 [JP] Japan ................... 2-178843

[51] Int. Cl.$^5$ ............... G01N 33/536; G01N 33/538
[52] U.S. Cl. ..................... 436/534; 73/61.71;
356/38; 356/39; 356/337; 356/338; 356/339;
356/341; 356/342; 356/343; 422/82.05;
435/808; 436/536; 436/538; 436/541; 436/805
[58] Field of Search ............... 73/53; 356/38, 39, 318,
356/337-343; 422/82.05; 436/534, 536, 538,
541, 805; 435/808

[56] References Cited

U.S. PATENT DOCUMENTS

| | | | |
|---|---|---|---|
| 3,088,875 | 5/1963 | Fisk | 436/534 |
| 3,710,279 | 1/1973 | Ashkin | 331/94.5 |
| 3,808,550 | 4/1974 | Ashkin | 331/94.5 |
| 4,537,861 | 8/1985 | Elings et al. | 436/519 |
| 4,661,460 | 4/1987 | Sakuma | 436/534 |
| 4,762,413 | 8/1988 | Namba et al. | 356/339 |
| 4,773,097 | 9/1988 | Suzaki et al. | 356/39 |
| 4,887,721 | 12/1989 | Martin et al. | 209/579 |
| 4,893,886 | 1/1990 | Ashkin et al. | 350/1 |
| 4,920,275 | 4/1990 | Itoh | 250/574 |

FOREIGN PATENT DOCUMENTS

| | | |
|---|---|---|
| 53-024015 | 3/1978 | Japan . |
| 54-108693 | 8/1979 | Japan . |
| 54-108694 | 8/1979 | Japan . |
| 54-108695 | 8/1979 | Japan . |
| 54-109494 | 8/1979 | Japan . |
| 58-187860 | 11/1983 | Japan . |
| 58187264 | 10/1984 | Japan . |
| 55159157 | 12/1986 | Japan . |

OTHER PUBLICATIONS

Patent Abstracts of Japan, vol. 7, No. 35 (P-175) [1180] (Kokai 57-189 067) Nov. 20, 1982.
Patent Abstracts of Japan, vol. 5, No. 36 (P-51) [708] (Kokai 55-159 157) Dec. 11, 1980.

*Primary Examiner*—David Saunders
*Assistant Examiner*—Christopher L. Chin
*Attorney, Agent, or Firm*—Fitzpatrick, Cella, Harper & Scinto

[57] ABSTRACT

A mixture is prepared by mixing carriers to which a substance specifically reacting on an object substance adheres with a sample containing the object substance. The mixture is irradiated by light having an intensity gradient to concentrate the carriers at and near the irradiated positions by the optical pressure of the light. The efficiency of an agglomeration reaction of the carriers is thereby increased. A qualitative or quantitative measurement of the object substance is performed by detecting a state of agglomeration of the carriers within the mixture.

20 Claims, 8 Drawing Sheets

SAMPLE MEASURING METHOD USING AGGLOMERATION REACTION OF MICROCARRIERS

BACKGROUND OF THE INVENTION

1. Field of the Invention

This invention relates to sample measurments, and more particularly, to measuring an object substance within a sample by generating and detecting an agglomeration reaction of microcarriers by specific coupling, such as an antigen-antibody reaction or the like.

2. Description of the Prior Art

A method of measuring an object substance within a sample with high accuracy utilizing a reaction of specifically coupling to the object substance, for example, an antigen-antibody reaction, so-called immunoassay, has been known. In one method, a reagent having a predetermined concentration containing a substance (for example, a monoclonal antibody), which is specifically coupled to an object substance (for example, a paticular antigen), adhered to the surfaces of carriers (for example, latex particles), serving as insoluble-fine particles, is prepared. The reagent is mixed with a sample, such as serum or the like, to agglomerate the carriers by an antigen-antibody reaction, and so-called incubation is performed wherein the carriers are left alone for a time period (usually, about 20-30 minutes) to allow a sufficient agglomeration reaction at a constant temperature. Subsequently, the object antigen in the serum is qualitatively or quantitatively measured by measuring the agglomeration state of the carriers mainly by an optical method. This method is described in detail in, for example, Japanese Patent Public Disclosure (Kokai) Nos. 53-24015 (1978), 54-108693 (1979), 54-108694 (1979), 54-108695 (1979), 54-109494 (1979), 55-159157 (1980) and 62-81567 (1987).

In the above-described conventional method, however, in the process wherein the carriers agglomerate to form clumps in incubation, contact between respective carriers is mainly caused by the Brownian movement of the carriers themselves. Hence, particularly when the concentration of the carriers in a reaction fluid is low, the reaction is inefficient, and much time is needed.

SUMMARY OF THE INVENTION

It is an object of the present invention to provide a method and apparatus which accelerates an agglomeration reaction of microcarriers.

It is another object of the present invention to provide a method and apparatus for measuring a reaction product agglomerated by the above-described method.

It is still another object of the present invention to provide a method and apparatus which can perform a reaction product measurement with high accuracy using image processing.

The invention is directed to sample processing in which carriers to which a substance reactive with an object substance adheres are mixed with a sample. The mixture is irradiated to concentrate the carriers whereby the efficiency of agglomeration is increased.

DETAILED DESCRIPTION OF THE PREFERRED EMBODIMENTS

Basic Principle

Figure 1A:
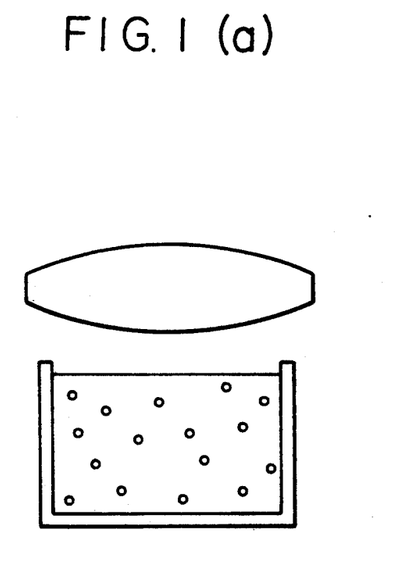
FIGS. 1a and 1b are diagrams illustrating the basic principle of the present invention.
Figure 1B:
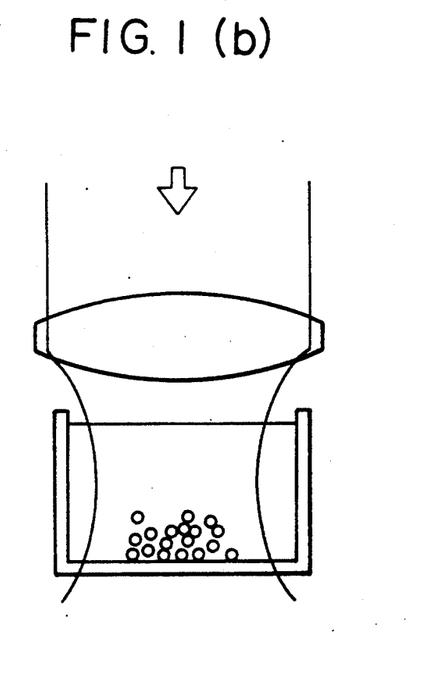

The basic principle of the present invention will be explained with reference to FIGS. 1($a$) and 1($b$). In general, when very fine particles are dispersed in a fluid as shown in FIG. 1($a$), if a beam waist is formed within the fluid using a light beam having a very high intensity and an intensity gradient, such as a laser light beam having a Gaussian distribution, a phenomenon is known to appear wherein a centripetal force due to the optical pressure of the laser light is exerted to collect the suspended fine particles near the center of the beam waist, as shown in FIG. 1($b$). This phenomenon is generally termed optical trapping, and is a useful method to move fine particles in a fluid to a particular place, or to collect them. The basic principle of the present invention resides in increasing a local density of carrier fine particles and thereby accelerating an agglomeration reaction by concentrating the particles at a beam waist portion utilizing the phenomenon of the optical trap. The speed and sensitivity in measurement are thereby increased.

First Embodiment

Figure 2:
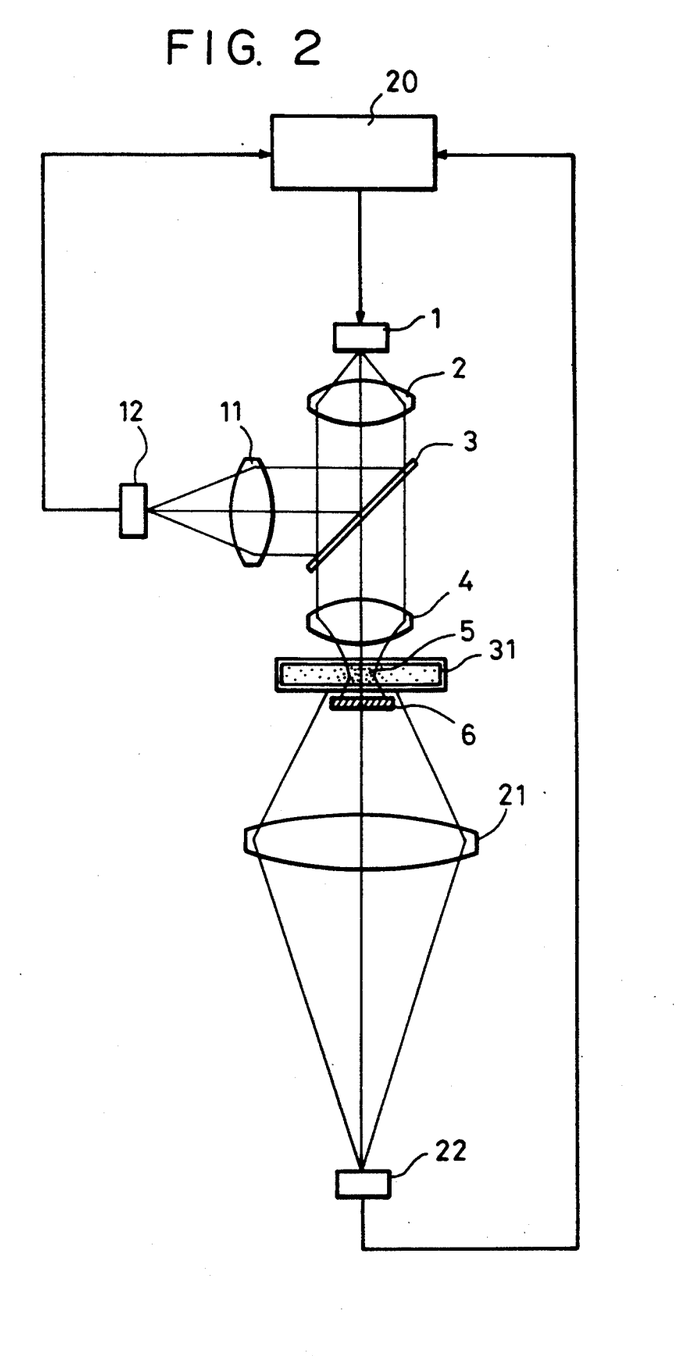
FIG. 2 shows an apparatus according to a first embodiment of the present invention.

A detailed explanation will now be provided of an apparatus of a first embodiment of the present invention with reference to the drawings. FIG. 2 shows the configuration of an apparatus of the first embodiment. In FIG. 2, a light source 1 emits illuminating light having an intensity gradient. In the present embodiment, a small, inexpensive semiconductor laser is used as the light source 1. A beam splitter 2 converts the light from the light source 1 into a parallel light beam. A beam splitter 3 is obliquely provided in the optical path. One of the light beams branching from the beam splitter 3 in condensed by a condenser lens 11, and the intensity of the condensed light beam is detected by a photodector 12. A control and arithmetic circuit 20 monitors the actual intensity of the light emitted from the light source 1 obtained from the photodector 12, and controls the amount of emission of the light source 1 so that the actual intensity equals a set intensity. Another light beam branching from the beam splitter 3 is condensed by a condenser lens 4 to form a beam waist having an intensity gradient in a portion 5 of a reaction cell 31 for detection. The reaction cell 31 is made of a material, such as transparent glass, plastic or the like, and has a structure such that a reaction sample is sealed within the cell. Where the light beam leaves the reaction cell 31, there is provided a light-tight light stopper 6, which cuts transmitted light passing through the reaction cell 31. By means of the light stopper 6, only scattered light generated at the portion 5 for detection of a substance suspended within the reaction sample is condensed by a condenser lens 21 to be incident upon a photodector 22, whose detection output is input to the control and arithmetic circuit 20.

The reaction sample sealed within the reaction cell 31 is prepared by mixing a reagent having a predetermined concentration and containing a monoclonal antibody, which tends to be specifically coupled to a particular target antigen, adhered to the surfaces of a large number of latex particles having a diameter of about 0.3 μm, with a sample (in general, blood components, or a body fluid, such as urine, saliva or the like). A detailed explanation thereof will be omitted, since such samples are described in detail in the above-described patent publications. The carriers are not limited to latex particles, but various kinds of fine particles may also be used. For example, glass particles, ceramic particles, kaolin, carbon black, microcapsules or the like may be used.

When a beam waist having an intensity gradient has been formed at the portion 5 for detection within the reaction cell 31, a large number of latex particles are collected near the center of the beam waist due to the phenomenon of optical trapping to increase the presence density, that is, the local concentration of latex particles. As a result, the probability of contact between the latex particles increases to accelerate the agglomeration of the latex particles via the target antigen within the serum. Thus, if the target antigen is present within the sample, the latex particles agglomerate to form a large number of clumps composed of about 2-5 particles. If the target antigen is absent, clumps are, of course, not formed.

Clumps are more easily formed as the size of used latex particles is smaller. However, if the size is too small, it becomes difficult to perform optical measurement due to the relationship with the wavelength of measuring light. While the size is set to 0.3 μm in the present embodiment, the size of about 0.1 μm-2.0 μm is generally preferred.

Heretofore, in order to generate the above-described agglomeration reaction of the latex particles, an accidental phenomenon, such as the Brownian movement, stirring or the like, has been utilized. Hence, the frequency of contact between latex particles is very small. As a result, in order to complete a sufficient agglomeration reaction of latex particles, incubation for a period as long as 20-30 minutes has been needed. To the contrary, in the present embodiment, since latex particles are concentrated near the center of the beam waist utilizing the above-described phenomenon of the optical trap to accelerate the agglomeration reaction of the latex particles, it is possible to shorten the time needed for incubation. Furthermore, the present embodiment also has the effect of increasing the sensitivity in measurement, since the agglomeration reaction is generated by increasing a local concentration utilizing the optical trap even if the total concentration of the latex particles is low.

If the above-described laser light is cut or the intensity of the light is reduced by a command from the control and arithmetic circuit 20 after thus accelerating the agglomeration reaction of the latex particles by continuously irradiating the light for a predetermined time period, the force of the optical trap is thereby reduced, and the latex particles concentrated near the beam waist are gradually dispersed within the entire fluid due to the Brownian movement and the like. At the time, the clumps of the latex particles formed by an antigen-antibody reaction are dispersed while preserving the clumps. If a stirring means or a vibration means is provided to stir or vibrate the fluid within the reaction cell 31 so that the dispersion is efficiently performed within a short time period, a more effective result may be obtained.

Subsequently, the degree of the agglomeration reaction of the latex particles within the sample for which incubation has been completed is measured. An explanation will now be provided of a measuring means for that purpose. In FIG. 2, the illuminating light for measuring the state of agglomeration is obtained by adjusting the intensity of the laser light emitted from the light source 1. The control and arithmetic circuit 20 sets the intensity of the laser light to an intensity which is sufficient for measuring a distribution of the latex particles and is not so strong as to form clumps of the latex particles by optical trapping.

The latex particles irradiated by the laser light generate peculiar scattered light in accordance with the state of agglomeration of the particles. Forwardly-scattered light of the scattered light directed in the forward direction of the optical path is condensed onto the photodetector 22 by the condenser lens 21. Data representing the degree of the agglomeration reaction of the latex particles are obtained from the detected intensity of the forwardly-scattered light. The output from the photodector 22 is input to the control and arithmetic circuit 20, which performs calculation for the analysis of the data. A more detailed method of analyzing data is described in, for example, Japanese Patent Public Disclosure (Kokai) No. 54-109494 (1979).

As another measuring method, after reducing the force of optical trapping by reducing the intensity of the laser light, the output from the photodetector 22 may be received a plurality of times every time a predetermined time period has lapsed, or output signals from the photodetector 22 are continuously detected to dynamically analyze the data, as described in the above-described patent publication.

The concentration of the target antigen can be obtained by comparing the result of measurement thus obtained with a working curve obtained by measuring a group of the target antigen having known concentrations in advance.

Latex particles and serum, serving as a sample, have their own peculiar characteristics of scattered light. Hence, data obtained by measuring in advance characteristics of scattered light from only latex particles, only serum, or a mixture fluid of the latex particles and the serum before the occurrence of the agglomeration reaction of the latex particles are stored in a memory as references, and the values of the data are subtracted from actually measured values as noise components. The references may be measured by the same apparatus before starting the optical trap, or may be extracted from data previously stored as data base in accordance with objects to be measured.

Second Embodiment

Figure 3:
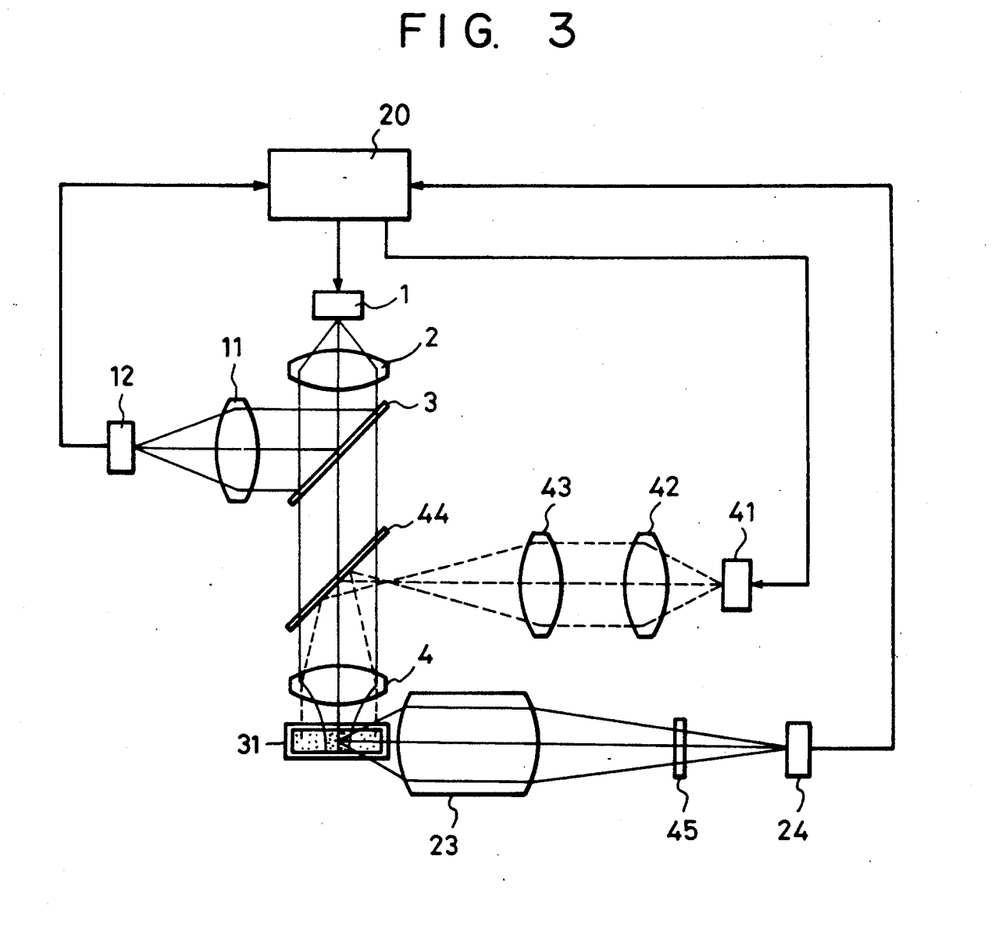
FIG. 3 shows an apparatus according to a second embodiment of the present invention.

An explanation will now be provided of a second embodiment of the present invention. FIG. 3 shows the configuration of an apparatus of the second embodiment. Numerals identical to those in FIG. 2 indicate identical or equivalent components.

In FIG. 3, a measuring light source 41 emits illuminating light for measurement, which has a wavelength different from that of the laser light from the above-described light source 1. A usual LED (light-emitting diode), and LED having high brightness, a semiconductor laser or the like is preferred as the light source 1 for the purpose of providing a small light source. However, the light source 1 is of course not limited to such a light source. A collimating lens 42 converts the illuminating light emitted from the measuring light source 41 into a parallel light beam. A condenser lens 43 illuminates the reaction cell 31 over a wide range. There is also shown a dichroic mirror 44. A band-pass filter 45 has characteristics of cutting the wavelength of the laser light originating from the light source 1 and selectively passing the wavelength of the light originating from the measuring light source 41.

While the forwardly-scattered light has been detected in the FIG. 2 embodiment, in the present embodiment, laterally-scattered light directed in lateral directions from the reaction cell 31 is condensed by a condenser lens 23, and is detected by a photodetector 24. Although, in the present embodiment, lateral directions are set to directions having an angle of 90 degrees relative to the optical axis of the illuminating light, the lateral directions are not limited to 90 degrees, but an arbitrary angle may be selected.

Next, an explanation will be provided of the operation of the above-described configuration. As in the FIG. 2 embodiment, the laser light from the light source 1 forms a beam waist having a high optical energy density at the portion 5 for detection within the reaction cell 31. After a predetermined time period wherein an agglomeration reaction of latex particles has been sufficiently performed, the light emission from the light source 1 is stopped. Although scattered light is generated by the laser light emitted from the light source 1, the system is arranged so that the light having the wavelength of the laser light is not incident upon the photodetector 24 by the function of the band-pass filter 45.

At the same time, the measuring light source 41 is also lit to provide illuminating light for measurement over a wide range within the reaction cell 31. At that time, the intensity of laterally-scattered light directed to lateral directions of the scattered light generated by the latex particles passes through the condenser lens 23 and the band-pass filter 45, and is detected by the photodetector 24. Since the light emitted from the measuring light source 41 does not form a beam waist within the reaction cell 31, the phenomenon of the optical trap does not occur. Hence, it becomes possible to freely set the intensity of the illuminating light to a value which is suitable for detecting the scattered light. Furthermore, since the wavelength of the light from the measuring light source 41 can be freely selected, it is possible to select a wavelength with which scattered light may be effectively generated by latex particles having a predetermined particle size.

In the present embodiment, the system is arranged so that the output from the photodetector 24, that is, the scattered light caused by the measuring light from the light source 41, is detected before irradiating the laser light from the light source 1, that is, before the agglomeration reaction is completed. The detected data are received as reference data. Subsequently, outputs from the photodetector 24 are time serially input to the control and arithmetic circuit 20, and the calculation of analysis is performed using a plurality of obtained data.

According to the present embodiment, since the light source for the optical trap and the light source for measurement are separately provided, and only scattered light caused by the light for measurement is detected by performing wavelength selection, it becomes possible to detect the scattered light to be measured in all the processes, and to perform a more detailed analysis.

Third Embodiment

Figure 4:
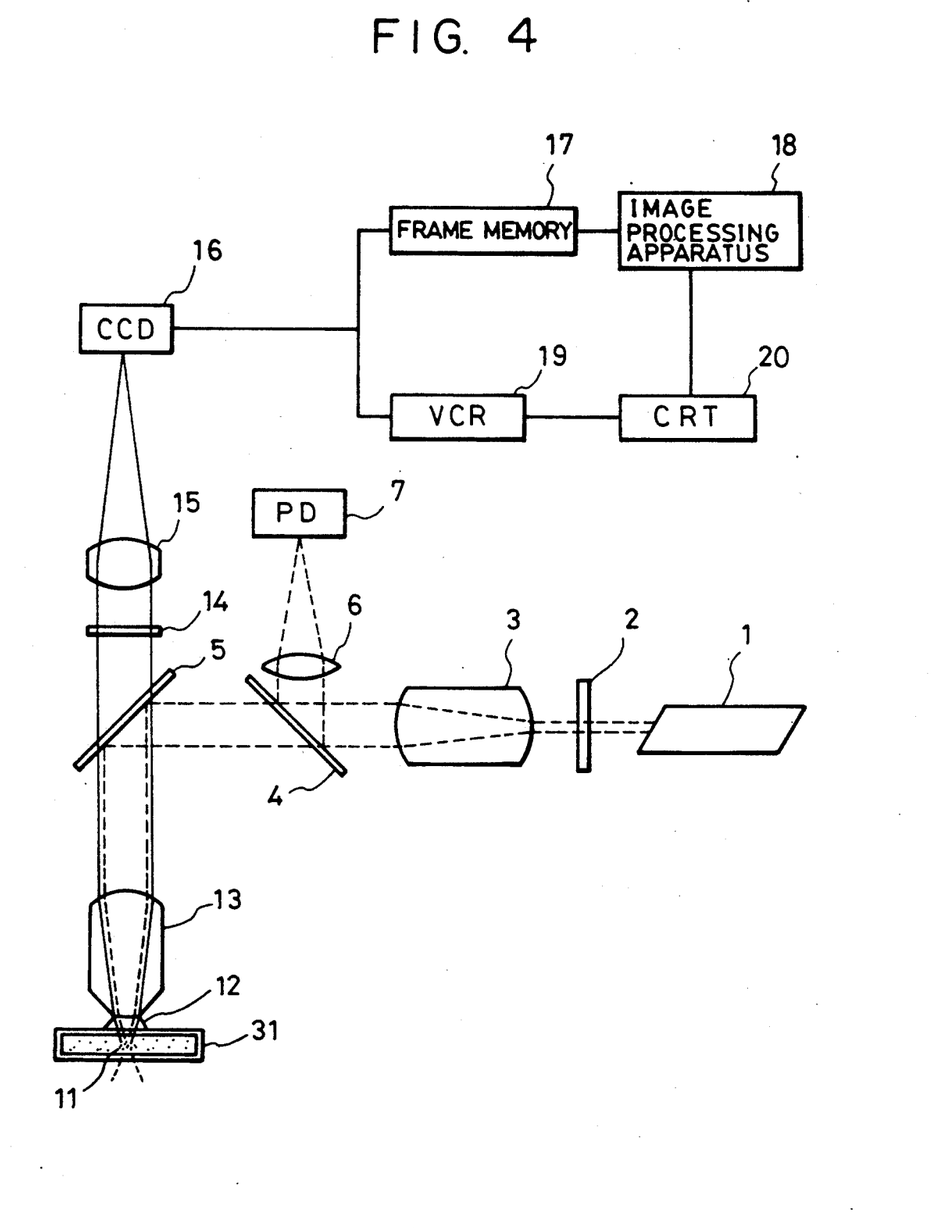
FIG. 4 shows an apparatus according to a third embodiment of the present invention.

A detailed explanation will now be provided of an apparatus according to a third embodiment of the present invention with reference to FIG. 4. In FIG. 4, a light source 1 emits irradiating light having an intensity gradient. In the present embodiment, a YAG laser having a wavelength of 1064 nm is used as the light source 1. There are shown a density filter 2, a beam expander 3, and a beam splitter 4 obliquely provided in the optical path. One of the light beams branching from the beam splitter 4 is condensed by a condenser lens 6, and the intensity of the condensed light is detected by a photodetector 7, A control circuit (not shown) monitors the actual intensity of the light emitted from the light source 1 obtained from the photodetector 7, and controls the amount of emission of the light source 1 so that the actual intensity equals a set intensity.

Another light beam branching from the beam splitter 4 is reflected by a dichroic mirror 5, and reaches an objective lens 13. The objective lens 13 is an immersion lens having a high numerical aperture (NA). In the present embodiment, NA=1.25. The laser light passing through the objective lens 13 passes through immersion oil 12, and forms a beam waist 11 having an intensity gradient at a portion for detection within a reaction cell 31. The reaction cell 31 is made of a material, such as transparent glass, plastic or the like, and has a structure so that a reaction sample is sealed within the cell.

The reaction sample sealed within the reaction cell 31 is prepared by mixing a reagent having a predetermined concentration and containing a monoclonal antibody, which tends to be specifically coupled to a particular target antigen, adhered to the surfaces of a large number of latex particles having a diameter of about 0.5 $\mu$m, with a sample (in general, blood components, or a body fluid, such as urine, saliva or the like). A detailed explanation thereof will be omitted, since such samples are described in detail in the above-described patent publications.

When the beam waist 11 having an intensity gradient has been formed at the portion 5 for detection within the reaction cell 31, a large number of latex particles are collected near the center of the beam waist 11 due to the phenomenon of optical trapping to increase the presence density, that is, the local concentration of latex particles. As a result, the probability of contact between the latex particles increases to accelerate the agglomeration of the latex particles via the target antigen within the serum. Thus, if the target antigen is present within the sample, the latex particles agglomerate to form a large number of clumps composed of about 2–5 particles. If the target antigen is absent, clumps are, of course, not formed.

Heretofore, in order to generate the above-described latex agglomeration reaction of the latex particles, an accidental phenomenon, such as the Brownian movement, stirring or the like, has been utilized. Hence, the frequency of contact between latex particles is very small. As a result, in order to complete a sufficient agglomeration reaction of latex particles, incubation for a period as long as 20–30 minutes has been needed. To the contrary, in the present embodiment, since latex particles are concentrated near the center of the beam waist utilizing the above-described phenomenon of the optical trap to accelerate the agglomeration reaction of the latex particles, it is possible to shorten the time needed for incubation. Furthermore, the present embodiment also has the effect of increasing the sensitivity in measurement, since the agglomeration reaction is generated by increasing a local concentration utilizing the optical trap even if the total concentration of the latex particles is low.

If the above-described laser light is cut or the intensity of the light is reduced by a command from a control circuit after thus accelerating the agglomeration reaction of the latex particles by continuously irradiating the light for a predetemined time period, the force of the optical trap is thereby reduce, and the latex particles concentrated near the beam waist are gradually dispersed within the entire fluid due to the Brownian movement and the like. At that time, the clumps of the latex particles formed by an antigen-antibody reaction are dispersed while preserving the clumps. If a stirring means or a vibration means is provided to stir or vibrate the fluid within the reaction cell 31 so that the dispersion is efficiently performed within a short time period, a more effective result may be obtained.

As the next step, the degree of the agglomeration reaction of the latex particles within the sample for which incubation has been completed is measured. An explanation of a measuring means for that purpose will now be described.

In FIG. 4 an image of latex particles illuminated by the visible light having a wavelength of 400 nm–800 nm by an illuminating optical system (not shown) is condensed by the objective lens 13, and reaches again the dichroic mirror 5. As described above, the dichroic mirror 5 has characteristics of reflecting the laser light having the wavelength of 1064 nm and transmitting the visible light. Hence, the above-described image of latex particles is transmitted through the dichroic mirror 5, passes through a density filter 14 and an eyepiece 15, and is imaged onto a two-dimensional imaging device (hereinafter termed a "CCD") 16, serving as a photosensor array.

Images signals for a plurality of images obtained by the CCD 16 are input to a digital frame memory 17 and a VCR (video cassette recorder) 19 to be stored as digital and analog image information, respectively. An image processing apparatus 18 performs image processing for analysis according to the contents of the frame memory 17. The result of the image processing is output to a CRT 20 or a printer (not shown). It is also possible to output the image recorded in the VCR 19 to the CRT 20. The system also has the function of first recording all images in the VCR 19, subsequently performing A/D conversion of reproduced output signals, and storing the converted signals in the frame memory 17. Thus, it is possible to repeatedly analyze images at various time periods with a minimum capacity of the frame memory.

Although, in the present embodiment, images of a sample are imaged using a two-dimensional photosensor array, a one-dimensional photosensor array may also be used to obtain substantially-two-dimensional image information by relatively moving the reaction cell and the photosensor array.

The above-desribed image processing apparatus 18 has mainly the following three image processing functions. These functions are selected by the operator.

(1) First Image Processing Function

A first image processing function is calculation of a product of two identical images while shifting the images, that is, a function to calculation of the autocorrelation of an image.

In general, if an amount of shift between two identical images is represented by $(\alpha, \beta)$, the two-dimensional autocorrelation function $\psi(\alpha, \beta)$ of the image is defined by:

$$\psi(\alpha, \beta) = \int \int_{-\infty}^{+\infty} f(x + \alpha, y + \beta) f(x, y) \, dx \, dy$$

When a large number of particles having a single diameter are randomly present on an image, the correlation function is expressed in the form of exp $(-\sqrt{\alpha^2+\beta^2}/\zeta)$ which has a maximum value when the distance $\sqrt{\alpha^2+\beta^2}=0$, and decreases as the value $\sqrt{\alpha^2+\beta^2}$ increases, where $\zeta$ is a parameter representing the particle size, and is termed a correlation distance. When latex particles do not agglomerate, the parameter $\zeta$ has a predetermined value $\zeta_1$ corresponding to the paticle size of latex particles. If $\alpha^2+\beta^2=\zeta_1^2$, the correlation function becomes 1/e. When latex particles agglomerate caused by an agglomeration reaction, it can be assumed that the particle size of latex particles has substantially increased. Hence, the correlation distance $\zeta_2$ has a value larger than the predetermined value $\zeta_1$.

Figure 7:
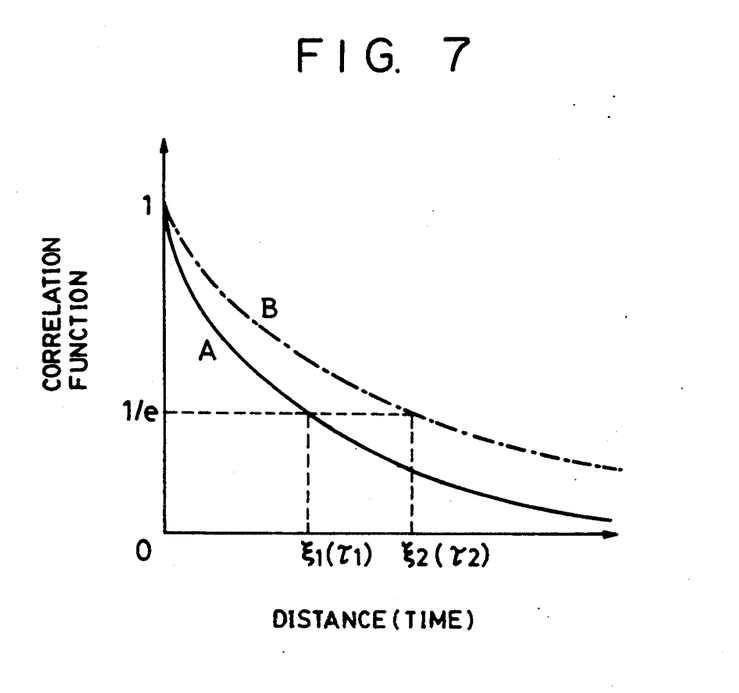
FIG. 7 is a graph showing a correlation relationship.

Such relationship is shown in FIG. 7, wherein solid curve A represents the correlation function when an agglomeration reaction of latex particles is not generated, and two-dot chain curve B represents the correlation function when an agglomeration reaction of latex particles is generated. As is apparent from FIG. 7, the degree of an agglomeration reaction of latex particles can be checked by obtaining the correlating $\zeta$ corresponding to the correlation function having a value of 1/e, or by obtaining a value of the correlation function when the two images are shifted by a predetermined distance $(\alpha, \beta)$.

More specifically, after forming the clumps of the latex particles by optical trapping and then reducing the intensity of the laser light, an image is received when the latex particles concentrated at one portion have been sufficiently dispersed, and the received image is binary-coded with a certain threshold value. Autoccorelation is obtained by calculating a product of two identical binary-coded images while shifting the positions of the images. Thus, the measurement of an object antigen can be performed from the degree of an agglomeration reaction of the latex particles.

(2) Second Image Processing Function

A second image processing function is calculation of a product of different images which change with time, that is, calculation of cross-correlation between images.

The cross-correlation function $\psi(t)$ having a parameter of time t is defined by:

$$\psi(t) = \int \int_{-\infty}^{+\infty} f(x, y, T + t) f(x, y, T) \, dx \, dy$$

When a large number of particles having a single diameter are present on an image, and the positions of the particles stochastically vary due to the Brownian movement and the like, the correlation function is expressed in the form of exp $(-t/\tau)$, which has a maximum value when time $t=0$ and decreases as time t increases, where $\tau$ is a parameter also representing the particle size, and is termed a correlation time. FIG. 7 shows such relationship.

More specifically, when the latex particles have been sufficiently dispersed after the lapse of a predetermined time after dissolving the optical trap by reducing the intensity of the above-described laser light, two images are received with a certain time interval, and the correlation function of the two images is calculated. The degree of the state of agglomeration of the latex particles is thereby obtained, and the measurement of a target antigen can be performed. In this case, however, since the correlation time $\tau$ also depends on the degree of position variations due to the Brownian movement and the like, it is desirable to perform temperature control of the reaction cell. It is more preferred to change the time interval for receiving images in accordance with temperature.

(3) Third Image Processing Function

A third image processing function utilizes the technique of contour extraction. As in the second image processing function, an image is received when the latex particles have been sufficiently dispersed after the lapse of a predetermined time after dissolving the optical trap by reducing the intensity of the laser light. The received image is binary-coded with a predetermined threshold value, and contour lines are extracted from the binary-coded image by image processing. The contour lines are approximated to circles. Since the radius of the circle is known as the radius of the latex particle, the approximation may be easily performed. At that time, contour lines which are smaller than the latex particle are removed as noise in the image. When an agglomeration reaction of the latex particles is generated, contour lines greater than the latex particle are produced. In this case, the contour lines are processed as the superposition of a plurality of circles. By statistically processing the areas, shapes and the like of contours obtained as a result of the above-described image processing, the number of the latex particles, the number of the latex particles agglomerated by an agglomeration reaction, the ratio of the two numbers, and the like within the image are obtained. The degree of the agglomeration reaction of the latex particles is thereby known, and the measurement of a target antigen can be performed.

Although an explanation has been provided of a method to approximate contour lines larger than the latex particle with a plurality of circles, a method to recognize the contour lines simply as a clump of the latex particles without performing approximation may also be used. This method has a feature of increasing the processing speed because an algorithm for image processing becomes very simple. Furthermore, although a binary-coding method has been shown as a method to extract contour lines, another method may be adopted wherein contour lines are obtained by differentiating the image and performing edge emphasis processing.

In the above-described first and third image processing functions, for the purpose of simplifying the explanation, an image received when a predetermined time has lapsed after reducing the intensity of the laser light is used. However, the number of images need not be limited to one. By continuously or intermittently performing measurement, it is possible to catch a change in time of the result of measurement, and to further improve reliability in measurement.

Similarly, also in the above-described second image processing function, it is possible to perform a more accurate measurement by time-serially and continuously receiving a plurality of images, and calculating cross-correlation between respective images.

In calculating autocorrelation and cross-correlation, it is not always necessary to use binary-coded images, but the calculation of the correlation function may be performed using multivalued halftone images received by a CCD.

Fourth Embodiment

Figure 5:
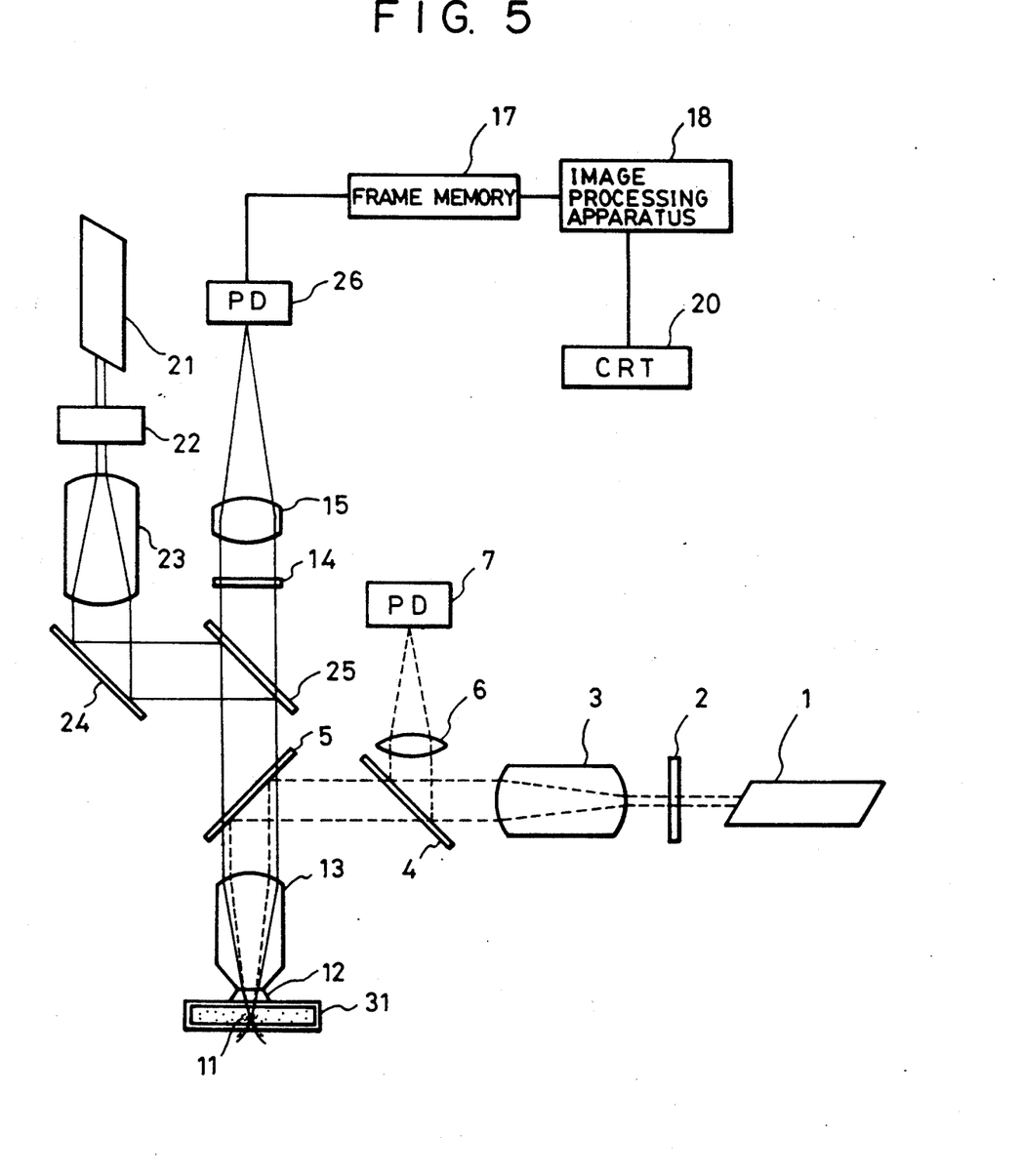
FIG. 5 shows an apparatus according to a fourth embodiment of the present invention.

A fourth embodiment of the present invention will now be explained with reference to FIG. 5. In FIG. 5, numerals identical to those in FIG. 4 indicate identical or similar components.

In the preceding embodiment, in order to obtain image information, an image within the measuring cell is imaged by the CCD, serving as the photosensor array. In the present embodiment, however, image information is obtained by performing two-dimensional optical scanning within the measuring cell with a fine light beam spot, and time-serially detecting generated light by a single photosensor.

The mechanism to accelerate the agglomeration reaction of the latex particles by the phenomenon of optical trapping is the same as in the forgoing FIG. 4 embodiment. The beam waist 11 is formed within the measuring cell 31 to accelerate the agglomeration reaction of the carriers.

As a laser light source 21, serving as a light source for scanning light, a semiconductor laser having a wavelength of, for example, 670 nm, which is different from the wavelength of the laser light source (YAG laser) 1 for the optical trap, is used. The laser light emitted from the laser light source 21 is scanned in the main-scanning direction by an acoustooptical device (hereinafter termed an "AOD") 22. After passing through a beam expander 23, the laser light is scanned in the subscanning direction orthogonal to the above-described main-scanning direction by a vibrating mirror 24. Thus, the combination of the AOD and the vibrating mirror constitutes a two-dimensional optical system.

Figure 6:
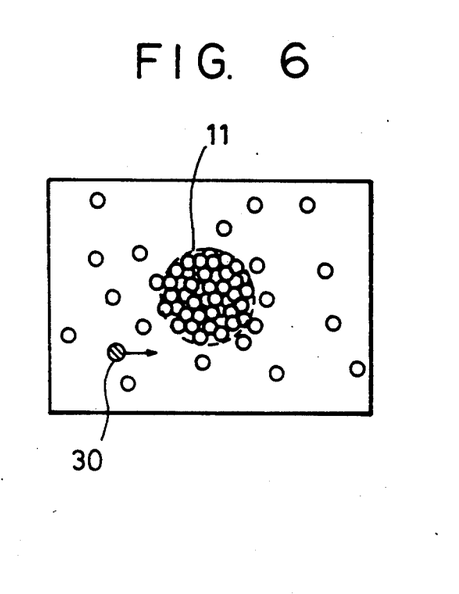
FIG. 6 illustrates how a light beam spot scans within a measuring cell.

The scanned light is directed in the direction of the measuring cell 31 by a half-mirror 25, then forms a fine imaged spot of about 0.5 $\mu$m within the measuring cell 31 by the objective lens 13, and performs two-dimensional optical scanning of the portion for measurement within the measuring cell 31 with the imaged spot. FIG. 6 shows the two-dimensional optical scanning. In FIG. 6, the latex particles are concentrated at the beam waist 11 of the laser light, and an imaged spot 30 performs two-dimensional scanning in the direction of the arrow.

Scattered light generated from the position irradiated by the imaged spot 30 at that time passes through the the band-pass filter 14 and the condenser lens 15, and is incident upon a photodetector 26 comprising a single photosensor. The output from the photodetector 26 is time-serially received in accordance with a synchronizing signal for controlling the above-described two-dimensional scanning optical system to be stored in the frame memory 17. Thus, two-dimensional image information which is substantially equivalent to that of the foregoing embodiment is obtained. The methods of analyzing the image information stored in the frame memory 17 are the same as in the foregoing embodiment. Image processing is performed in the image processing apparatus 18 by an analyzing method selected by the operator.

Fifth Embodiment

Figure 8:
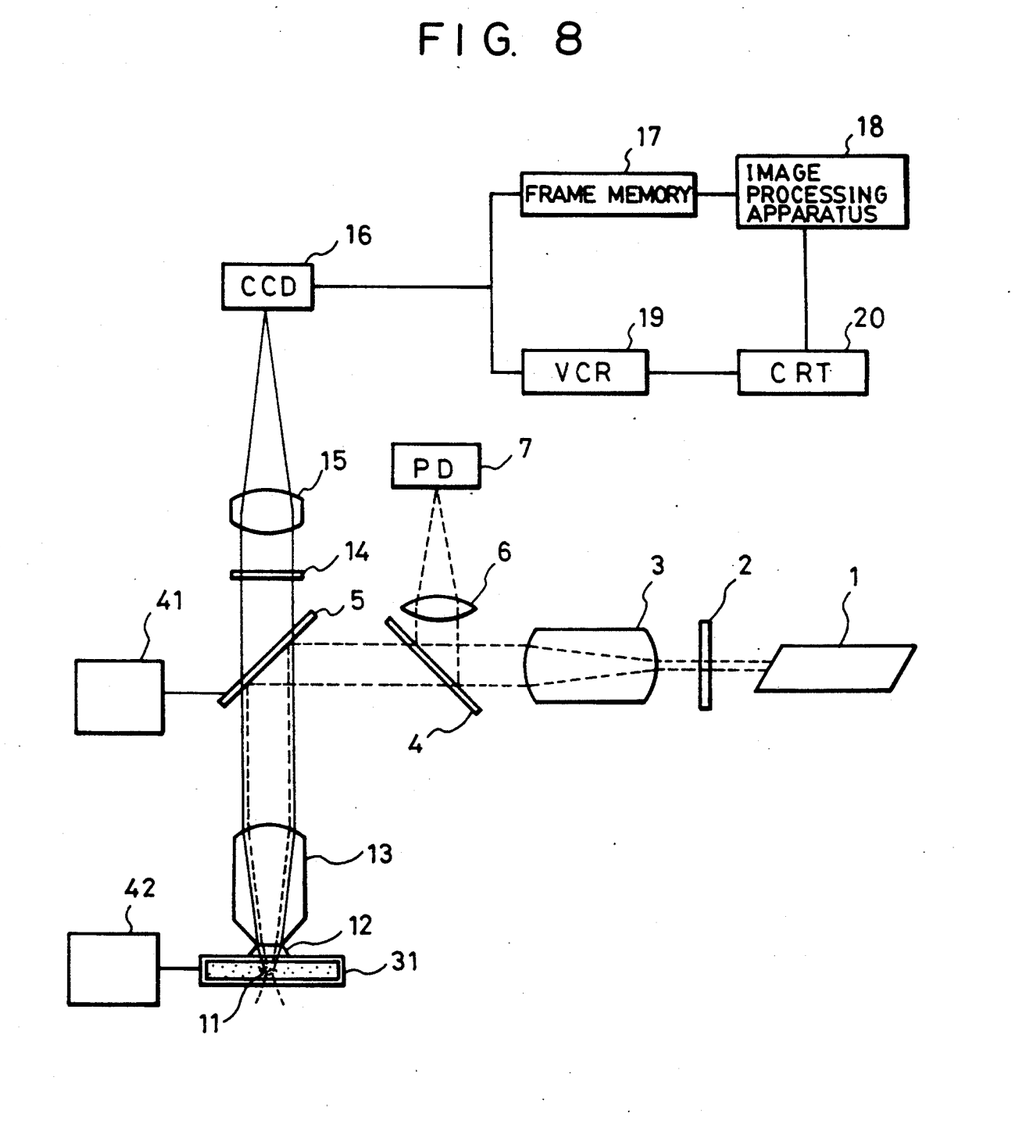
FIG. 8 shows an apparatus according to a fifth embodiment of the present invention.

An explanation will now be provided of an apparatus according to a fifth embodiment of the present invention with reference to FIG. 8, which is substantially identical to FIG. 4. In FIG. 8, the same numerals as in FIG. 4 indicate the same components.

In the present embodiment, in order to generate an agglomeration reaction over a wide range, a swinging mechanism 41 is provided for the dichroic mirror 5, and a vibration mechanism 42 is provided for the reaction cell 31. By swinging the dichroic mirror 5, the swinging mechanism 41 one-dimensionally scans the beam waist 11 within the reaction cell 31. The vibration mechanism 42 one-dimensionally vibrates the reaction 31 in a direction substantially orthogonal to the scanning direction. It is thereby possible to two-dimensionally change the positional relationship between the beam waist 11 and a reaction sample sealed within the reaction cell 31.

Alternatively, by making one of the vibration mechanism 42 and the swinging mechanism 41 vibrate in two dimensions, the reaction cell 31 may be two-dimensionally vibrated on a plane perpendicular to the irradiating optical axis. Furthermore, by repeatedly turning on and off the above-described $Nd^{3+}$ laser light with a predetermined period in synchronization with the two-dimensional scanning of the beam waist 11, light illumination for the optical trap may be performed at substantially plural fixed positions.

When the beam waist 11 having an intensity gradient is formed at a portion for detection within the reaction cell 31, a large number of latex particles are collected near the center of the beam waist 11 due to the phenomenon of optical trapping to increase the presence density, that is, the local concentration of the latex particles. As a result, the probability of contact between the latex particles increases to accelerate the agglomeration of the latex particles via a target antigen within serum. Thus, if the target antigen is present within the sample, the latex particles agglomerate to form a large number of clumps composed of about 2–5 particles. If the target antigen is absent, clumps are, of course, not formed. In the present embodiment, since the beam waist 11 is moved two-dimensionally within the reaction sample sealed in the reaction cell 31, latex particles present in a wider range of movement of the beam are irradiated with the light. As a result, a larger number of latex particles present on the locus of the beam waist 11 can be collected by the optical trap.

As described above, according to the present embodiment, in increasing the efficiency of an agglomeration reaction utilizing the optical trapping phenomenon, the optical trapping is generated over a wider range by relatively changing the position of light irradiation for the sample. It is thereby possible to further accelerate the agglomeration reaction.

Sixth Embodiment

An explanation will now be provided of a sixth embodiment of the present invention wherein the state of agglomeration of carriers is measured using the technique of flow cytometry.

Figure 9:
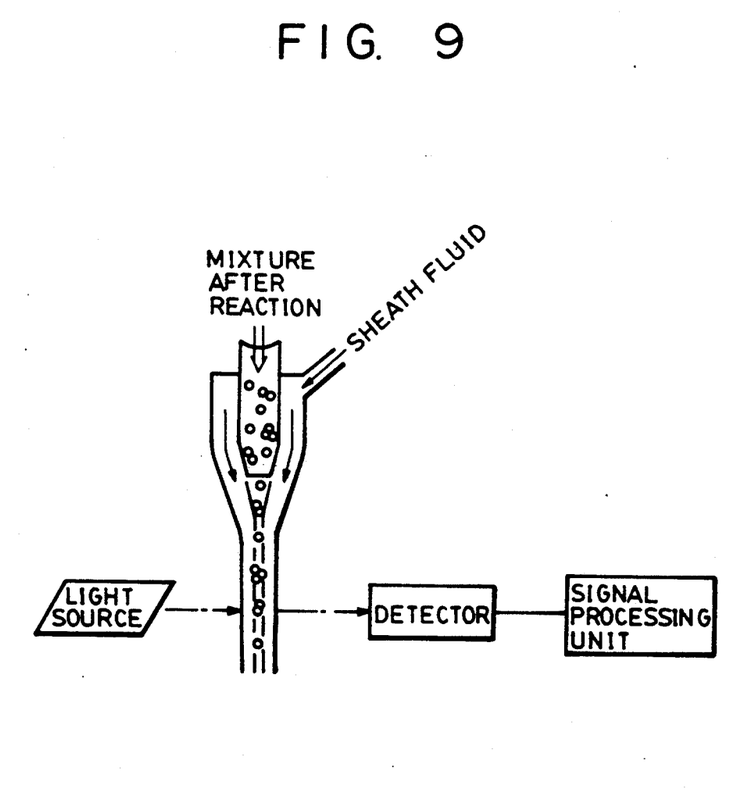
FIG. 9 shows an apparatus according to a sixth embodiment of the present invention.

As preprocessing, incubation according to the method shown in FIG. 1 is performed to generate an agglomeration reaction. Latex particles or clumps of latex particles are individually separated from the obtained mixture after the reaction, and are floated within a fine tube by a laminar sheath flow principle in an apparatus as shown in FIG. 9. The state of agglomeration of latex particles is measured by irradiating light onto an individual particle and measuring generated scattered light, transmitted light, fluorescence or the like. The details of this measuring method are described in, for example, Japanese Patent Public Disclosure (Kokai) Nos. 60-111963 (1985) and 1-207663 (1989). Contrary to the method to detect the entire tendency of agglomeration by simultaneously irradiating light onto a plurality of carriers as in the foregoing embodiment, the present method detects the agglomeration of individual particles. Hence, it is possible to discriminate a more detailed state of agglomeration, and to perform measurement with high accuracy. Furthermore, according to the method of Japanese Patent Public Disclosure (Kokai) No. 1-207663 (1989), the efficiency of measurement is further increased since antigens of different kinds can be discriminated in one measurement.

The state of agglutination of flowing particles may not necessarily be measured by an optical method, but by a so-called Coulter sizing method wherein the size of a passing individual particle is measured by detecting a change in electric impedance.

The invention has been described with reference to particular illustrative embodiments. It is apparent to those skilled in the art that various modifications may be made without departing from the spirit and scope of the invention. In the present invention, the method of measuring a state of agglomeration is not limited to the measurement of scattered light as in the foregoing embodiments, but various measuring methods may also be used, such as a method by detecting a change in turbidity, that is, a change in transmittance or absorbance, as described in Japanese Patent Public Disclosure (Kokai) Nos. 58-187860 (1983) and 58-96251 (1983), a method using an integrating sphere as shown in Japanese Patent Public Disclosure (Kokai) No. 59-187264 (1984), a method utilizing the fluctuation of light, a method utilizing photoacoustics, and the like.

What is claimed is:

1. A sample processing method comprising:
   preparing a mixture by mixing carriers to which is adhered a substance that specifically binds to an object substance, with a sample containing said object substance; and
   directing light having an intensity gradient onto said mixture to concentrate said carriers at positions irradiated by the light, thereby increasing the efficiency of an agglomeration reaction of said carriers.

2. A method according to claim 1, further comprising the step of relatively changing the position irradiated by the light in said mixture.

3. A method according to claim 1, wherein said light comprises a laser light.

4. A method according to claim 1, wherein said carriers comprise insoluble fine particles.

5. A method according to claim 4, wherein said insoluble fine particles comprise latex particles.

6. A method according to claim 1, wherein said substance adhered to the carriers comprises an antibody specific for an object antigen.

7. A method according to claim 1, wherein said sample comprises a blood sample.

8. A sample measuring method comprising:
   preparing a mixture by mixing carriers to which is adhered a substance that specifically binds to an object substance, with a sample containing said object substance;
   directing light having an intensity gradient onto said mixture to concentrate said carriers at positions irradiated by the light, thereby increasing the efficiency of an agglomeration reaction of said carriers; and detecting a state of agglomeration of the carriers within said mixture to perform a measurement of the object substance.

9. A method according to claim 8, wherein the detection of said state of agglomeration comprises optical detection.

10. A method according to claim 8, wherein said light comprises a laser light.

11. A method according to claim 8, wherein said carriers comprise latex particles.

12. A method according to claim 8 wherein said substance adhered to the carriers comprises an antibody specific for an object antigen.

13. A sample measuring method comprising:
preparing a mixture by mixing carriers, to which is adhered a substance that specifically binds to an object substance, with a sample containing said object substance;
directing light having an intensity gradient onto said mixture to concentrate said carriers at positions irradiated by the light, thereby increasing the efficiency of an agglomeration reaction of said carriers; and
detecting a state of agglomeration of the carriers within said mixture, to perform a measurement of said object substance, wherein said detecting comprises obtaining image information at the completion of the agglomeration reaction for image analysis.

14. A method according to claim 13, wherein the detection of said image information comprises detecting an image of the sample by a photosensor array.

15. A method according to claim 13, wherein the detection of said image information comprises detecting an image by performing two-dimensional optical scanning of the sample.

16. A method according to claim 13, wherein the analysis of said image information uses an image obtained by binary-coding a detected image with predetermined threshold value.

17. A method according to claim 13, wherein the analysis of said image information comprises calculating the degree of said agglomeration by calculating an autocorrelation of a detected image.

18. A method according to claim 13, wherein the analysis of said image information comprises calculating a degree of said agglomeration by extracting contours of a detected image.

19. A method according to claim 13, further comprising the step of changing the positions irradiated by the light in said mixture.

20. A method according to claim 13, wherein said light comprises a laser light.

* * * * *

UNITED STATES PATENT AND TRADEMARK OFFICE
CERTIFICATE OF CORRECTION

PATENT NO. : 5,198,369
DATED : March 30, 1993
INVENTOR(S) : YUUJI ITOH ET AL.

It is certified that error appears in the above-identified patent and that said Letters Patent is hereby corrected as shown below:

On title page,

AT [75] INVENTORS

"Yuuji Itoh; Michiyo Itoh," should read
--Yuuji Itoh represented by Michiyo Itoh,--.

AT [56] REFERENCES CITED

Foreign Patent Documents, "58187264  10/1984  Japan
                           55159157  12/1986  Japan"
should read --59-187264  10/1984  Japan
              55-159157  12/1980  Japan--.

COLUMN 1

Line 21, "paticular" should read --particular--.

COLUMN 3

Line 22, "ence" should read --ent--.

COLUMN 7

Line 10, "reduce," should read --reduced,--.
Line 25, "FIG. 4" should read --FIG. 4,--.
Line 38, "Images" should read --Image--.

COLUMN 8

Line 32, "correlating" should read
         --correlation distance--.

UNITED STATES PATENT AND TRADEMARK OFFICE
CERTIFICATE OF CORRECTION

PATENT NO. : 5,198,369
DATED : March 30, 1993
INVENTOR(S) : YUUJI ITOH ET AL.

It is certified that error appears in the above-identified patent and that said Letters Patent is hereby corrected as shown below:

COLUMN 10

Line 51, "the" (first occurrence) should be deleted.

COLUMN 12

Line 36, "carriers" should read --carriers,--.
Line 60, "carriers" should read --carriers,--.

COLUMM 13

Line 10, "claim 8" should read --claim 8,--.

Signed and Sealed this

Sixteenth Day of November, 1993

Attest:

BRUCE LEHMAN

Attesting Officer   Commissioner of Patents and Trademarks